United States Patent
Olek et al.

(10) Patent No.: US 9,719,131 B2
(45) Date of Patent: Aug. 1, 2017

(54) METHOD FOR DETERMINING THE DEGREE OF METHYLATION OF DEFINED CYTOSINES IN GENOMIC DNA IN THE SEQUENCE CONTEXT OF 5'-CPG-3'

(75) Inventors: Alexander Olek, Berlin (DE); Christian Piepenbrock, Berlin (DE); Kurt Berlin, Stahnsdorf (DE); David Guetig, Berlin (DE)

(73) Assignee: EPIGENOMICS AG, Berlin (DE)

( * ) Notice: Subject to any disclaimer, the term of this patent is extended or adjusted under 35 U.S.C. 154(b) by 0 days.

(21) Appl. No.: 12/847,005

(22) Filed: Jul. 30, 2010

(65) Prior Publication Data
US 2011/0136687 A1   Jun. 9, 2011

Related U.S. Application Data

(63) Continuation of application No. 10/363,345, filed as application No. PCT/EP01/10074 on Sep. 1, 2001, now abandoned.

(30) Foreign Application Priority Data

Sep. 1, 2000 (DE) .................. 100 43 826
Sep. 5, 2000 (DE) .................. 100 44 543

(51) Int. Cl.
C07H 21/02 (2006.01)
C12Q 1/68 (2006.01)

(52) U.S. Cl.
CPC ......... *C12Q 1/6827* (2013.01); *C12Q 1/6883* (2013.01); *C12Q 2600/154* (2013.01)

(58) Field of Classification Search
CPC ............... C12Q 1/6827; C12Q 1/6883; C12Q 2600/154
See application file for complete search history.

(56) References Cited

U.S. PATENT DOCUMENTS

| 5,985,551 A | * | 11/1999 | Brennan | ............. 435/6.11 |
| 6,214,556 B1 | | 4/2001 | Olek et al. | |
| 2003/0165823 A1 | | 9/2003 | Cronin et al. | |

FOREIGN PATENT DOCUMENTS

| CA | 2310384 | 5/2007 |
| DE | 19754482 | 7/1999 |
| WO | 9511995 | 5/1995 |
| WO | 9826095 | 6/1998 |
| WO | 9954461 | 10/1999 |
| WO | 0044934 | 8/2000 |
| WO | 0168911 | 9/2001 |

OTHER PUBLICATIONS

Wong D.J. et al. Cancer Research (1997) vol. 57, pp. 2619-2622.*
Ahen H. The Scientist (Jul. 24, 1995) pp. 20 and 22.*
Cordier C. et al. Eur. J. Biochem. 261, 722-733 (1999).*
Raineri I. et al. Nucleic Acids Research, vol. 19, No. 14, p. 4010.*
GenBank Locus: BG772557 (May 15, 2001), from www.ncbi.nlm.gov, 2 pritned pages.*
NCBI Blast: 12693 result, alignment of SEQ ID No. 12693 and NG_011683.1, from blast.ncbi.nlm.nih.gov, 1 printed page from Aug. 18, 2015.*
Strausberg R.L. et al. Science (Oct. 15, 1999) vol. 286, pp. 455-457.*
"602720653F1 NIH_MGC_97 *Homo sapiens* cDNA clone IMAGE:4837716 5-, mRNA sequence" (May 14, 2001) from www.ncbi.nlm.nih.gov, pp. 1-2.*
Meldrum D. Genome Res. 2000;10(9):1288-1303.*
Armstrong et al. (Jun. 1, 2000) "Suspension arrays for high throughput, multiplexed single nucleotide polymorphism genotyping," Cytometry. 40(2):102-8.
Behr et al. (May 28, 1999) "Comparative genomics of BCG vaccines by whole-genome DNA microarray," Science. 284(5419):1520-3.
Belinsky et al. (Sep. 29, 1998) "Aberrant methylation of p16(1NK4a) is an early event in lung cancer and a potential biomarker for early diagnosis," Proc Natl Acad Sci. 95(20):11891-6.
Eads et al. (Apr. 15, 2000) "MethyLight: a high-throughput assay to measure DNA methylation," Nucleic Acids Res. 28(8):E32i-viii.
Genbank Accession AF089750 (Mar. 29, 2000) "*Homo sapiens* flotillin-1 mRNA," complete cds, p. 1-2.
Gentalen et al. (Mar. 15, 1999) "A novel method for determining linkage between DNA sequences: hybridization to paired probe arrays," Nucleic Acids Res. 27(6):1485-91.
Gonzalgo et al. (Jun. 15, 1997) "Rapid quantitation of methylation differences at specific sites using methylation-sensitive single nucleotide primer extension (Ms-SNuPE)," Nucleic Acids Res. 25(12):2529-2531.
Grunau et al. (Jul. 1, 2001) "Bisulfite genomic sequencing: systematic investigation of critical experimental parameters," Nucleic Acids Res. 29(13):E65-5.
Herman et al. (1996) "Methylation-specific PCR: A novel PCR assay for methylation status of CpG islands," Proc. Natl. Acad. Sci. 93:9821-6.

(Continued)

*Primary Examiner* — Stephen Kapushoc
(74) *Attorney, Agent, or Firm* — Lathrop & Gage, LLP; James H. Velema, Esq.; Sean M. Coughlin, Esq.

(57) ABSTRACT

A method is described for the detection of the degree of methylation of a specific cytosine in the sequence context 5'-CpG-3' of a genomic DNA sample. In the first step, the genomic DNA is chemically treated in such a way that the cytosine bases are converted to uracil, but not the 5-methylcytosine bases. Then segments of the genomic DNA which contain the said specific cytosine are amplified, whereby the amplified products are given a detectable label and in the following steps the extent of hybridization of the amplified products on two classes of oligonucleotides is determined by detection of the label of the amplified products, and a conclusion is made on the extent of methylation of said specific cytosine in the genomic DNA sample from the ratio of the labels detected on the two classes of oligonucleotides as a consequence of the hybridization.

7 Claims, 2 Drawing Sheets

(56) References Cited

OTHER PUBLICATIONS

Nagane et al. (Apr. 2000) "PCR amplification in bisulfite methylcytosine mapping in the GC-rich promoter region of amyloid precursor protein gene in autopsy human brain," Brain Res Brain Res Protoc. 5(2):167-71. [Abstract].

Niemeyer et al. (1999) "DNA Microarrays," Angew. Chem. Int. Ed. 38(19):2865-9.

Park et al. (May 2000) "A latex bead-based flow cytometric immunoassay capable of simultaneous typing of multiple pneumococcal serotypes (Multibead assay)," Clin Diagn Lab Immunol. 7(3):486-9.

Peng et al. (Jul. 1994) "Multiple PCR analyses on trace amounts of DNA extracted from fresh and paraffin wax embedded tissues after random hexamer primer PCR amplification," J Clin Pathol. 47(7):605-8.

Rajeevan et al. (Mar. 1999) "Chemiluminescent analysis of gene expression on high-density filter arrays," J Histochem Cytochem. 47(3):337-42.

Rein et al. (1998) "Identifying 5-methylcytosine and related modifications in DNA genomes," Nucleic Acids Research. 26(10):2255-64.

Richmond et al. (Oct. 1, 1999) "Genome-wide expression profiling in *Escherichia coli* K-12," Nucleic Acids Res. 27(19):3821-35.

Tsuneyoshi et al. (1997) "Mass spectrometric gene diagnosis of one-base substitution from polymerase chain reaction amplified human DNA," Rapid Commun Mass Spectrom. 11(7):719-22. [Abstract].

Umezawa et al. (Sep. 1997) "Methylation of an ETS site in the intron enhancer of the keratin 18 gene participates in tissue-specific repression," Mol Cell Biol. 17(9):4885-94.

Volonte et al. (1999) "Flotillins/Cavatellins Are Differentially Expressed in Cells and Tissues and Form a Hetero-oligomeric Complex with Caveolins in Vivo," J. Biol. Chem. 274(18):12702-9.

Yan et al. (Apr. 2000) "CpG island arrays: an application toward deciphering epigenetic signatures of breast cancer," Clin Cancer Res. 6(4):1432-8.

Yuan et al. (Jul. 1, 1999) "Isolation of a novel gene, TSP50, by a hypomethylated DNA fragment in human breast cancer," Cancer Res. 59(13):3215-21.

International Search Report corresponding to International Patent Application No. PCT/EP2001/010074, mailed Nov. 4, 2003.

* cited by examiner

C

B

A

METHOD FOR DETERMINING THE DEGREE OF METHYLATION OF DEFINED CYTOSINES IN GENOMIC DNA IN THE SEQUENCE CONTEXT OF 5'-CPG-3'

CROSS-REFERENCE TO RELATED APPLICATIONS

This application is a Continuation of U.S. patent application Ser. No. 10/363,345 filed Mar. 3, 2003, which is the U.S. 371 nationalization of PCT/EP01/10074 filed Sep. 1, 2001 now abandoned (WO 02/018632 published Mar. 7, 2002), which claims priority to German Patent Application Nos. DE10043826.1 filed Sep. 1, 2000, and DE10044543.8 filed Sep. 5, 2000, all of which are incorporated herein by reference in their entireties.

FIELD OF THE INVENTION

The invention concerns a method for the detection of the degree of methylation of a specific cytosine in the sequence context 5'-CpG-3' of a genomic DNA sample.

SEQUENCE LISTING

A Sequence Listing comprising 40,723 SEQ ID NOS and attached as part of this application is incorporated herein by reference.

The levels of observation that have been well studied in molecular biology according to developments in methods in recent years include the genes themselves, the transcription of these genes into RNA and the translation to proteins therefrom. During the course of development of an individual, which gene is turned on and how the activation and inhibition of certain genes in certain cells and tissues are controlled can be correlated with the extent and nature of the methylation of the genes or of the genome. In this regard, pathogenic states are also expressed by a modified methylation pattern of individual genes or of the genome.

The present invention describes a method with which many cytosine bases in a given DNA sample can be investigated simultaneously for the presence of a methyl group at position 5 by means of hybridization. It also describes nucleic acids, oligonucleotides and PNA oligomers which are useful in order to employ the method for the diagnosis of existing diseases or of predisposition for diseases.

5-Methylcytosine is the most frequent covalently modified base in the DNA of eukaryotic cells. For example, it plays a role in the regulation of transcription, in genetic imprinting and in tumorigenesis. The identification of 5-methylcytosine as a component of genetic information is thus of considerable interest. 5-Methylcytosine positions, however, cannot be identified by sequencing, since 5-methylcytosine has the same base-pairing behavior as cytosine. In addition, in the case of a PCR amplification, the epigenetic information which is borne by the 5-methylcytosines is completely lost.

The methylation of CpG islands is often equated with transcription inactivity. Although there is clear evidence that CpG islands are to be found in promoters of genes, not all CpG islands and methylation sites are localized in known promoters. In various tissue-specific and imprinting genes, the CpG islands are localized at considerable distance downstream of the start of transcription, and also many genes possess multiple promoters. Methylation of CpG dinucleotides has been detected as a causal factor for a number of diseases. In contrast to classical mutations, DNA methylation involves a mechanism, which describes a substitution on the base without modifying the coding function of a gene. This interplay between epigenetic modification and classical mutations plays an important role in tumorigenesis. For example, focal hypermethylation and generalized genomic demethylation are features of many different tumor types. It is assumed that tumorigenesis and tumor progression are caused, first of all, by hypermethylation of induced mutation events, and secondly, by the turning off of genes which control cellular proliferation, and/or the induced reactivation of genes, which are used only for embryological development, via demethylation.

In hereditable non-polyposis colorectal cancer, e.g., the majority of mutation-negative cases of colon cancer are based rather on the hypermethylation of the hMLH1 promoter and the associated non-expression of hMLH1, a repair gene for erroneous base pairings (Bevilacqua R A, Simpson A J, Methylation of the hMLH1 promoter but no hMLH1 mutations in sporadic gastric carcinomas with high-level microsatellite instability. Int J Cancer. 2000 Jul. 15; 87(2): 200-3). In the pathogenesis of lung cancer, the loss of expression is correlated with the methylation of CpG islands in the promoter sequence of an RAS effector homolog. (Dammann R, Li C, Yoon J H, Chin P L, Bates S, Pfeifer G P, Nucleotide. Epigenetic inactivation of a RAS association domain family protein from the lung tumour suppressor locus 3p21.3. Nat Genet. 2000 July; 25(3):315-9). An epigenetic inactivation of the LKB1 tumor supressor gene, including the hypermethylation of the promoter, is associated with the Peutz-Jeghers syndrome (Esteller M, Avizienyte E, Corn P G, Lothe R A, Baylin S B, Aaltonen L A, Herman J G, Epigenetic inactivation of LKB1 in primary tumors associated with the Peutz-Jeghers syndrome. Oncogene. 2000 Jan. 6; 19(1):164-8).

A plurality of diseases, which are associated with methylation, have in their etiology a close connection with the tumor suppressor genes p16 or p15. Thus a relationship between Mycosis fungoides and hypermethylation of the p16(INK4a) gene is assumed (Navas I C, Ortiz-Romero P L, Villuendas R, Martinez P, Garcia C, Gomez E, Rodriguez J L, Garcia D, Vanaclocha F, Iglesias L, Piris M A, Algara P, p16(INK4a) gene alterations are frequent in lesions of mycosis fungoides. Am J Pathol. 2000 May; 156(5):1565-72). Also, there is a strong correlation between the turning off of the transcription of the p16 gene in gastric carcinoma and the de novo methylation of a few specific CpG sites (Song S H, Jong H S, Choi H H, Kang S H, Ryu M H, Kim N K, Kim W H, Bang Y J, Methylation of specific CpG sites in the promoter region could significantly down-regulate p16(INK4a) expression in gastric adenocarcinoma. Int J Cancer. 2000 Jul. 15; 87(2):236-40). The pathogenesis of cholangiocarcinoma, which is associated with primary sclerosing cholangitis, has been related to the inactivation of the p16 tumor suppressor gene, which is again dependent on the methylation of the p16 promoter (Ahrendt S A, Eisenberger C F, Yip L, Rashid A, Chow J T, Pitt H A, Sidransky D, Chromosome 9p21 loss and p16 inactivation in primary sclerosing cholangitis-associated cholangiocarcinoma. J Surg Res. 1999 Jun. 1; 84(1):88-93). The inactivation of the p16 gene by hypermethylation plays a role in the genesis of leukemia and in the progression of acute lymphoblastic leukemia (Nakamura M, Sugita K, Inukai T, Goi K, Iijima K, Tezuka T, Kojika S, Shiraishi K, Miyamoto N, Karakida N, Kagami K, O-Koyama T, Mori T, Nakazawa S, p16/MTS1/INK4A gene is frequently inactivated by hypermethylation in childhood acute lymphoblastic leukemia with 11q23 translocation. Leukemia. 1999 June; 13(6):884-90).

In addition, it is postulated that the hypermethylation of the p16 and p15 genes plays a decisive role in the tumorigenesis of multiple myeloma (Ng M H, Wong I H, Lo K W, DNA methylation changes and multiple myeloma. Leuk Lymphoma. 1999 August; 34(5-6):463-72). The VHL gene, which is inactivated by methylation, appears to participate in predisposition to renal carcinoma (Glavac D, Ravnik-Glavac M, Ovcak Z, Masera A, Genetic changes in the origin and development of renal cell carcinoma (RCC). Pflugers Arch. 1996; 431(6 Suppl 2):R193-4). A divergent methylation of the 5'-CpG island may participate in nasopharyngeal carcinoma, possibly by the inactivation of transcription of the p16 gene (Lo K W, Cheung S T, Leung S F, van Hassett A, Tsang Y S, Mak K F, Chung Y F, Woo J K, Lee J C, Huang D P, Hypermethylation of the p16 gene in nasopharyngeal carcinoma. Cancer Res. 1996 Jun. 15; 56(12):2721-5). An inactivation of the p16 protein was detected in liver cell carcinoma. Promoter hypermethylation and homozygous deletions are the most frequent mechanisms here (Jin M, Piao Z, Kim N G, Park C, Shin E C, Park J H, Jung H J, Kim C G, Kim H, p16 is a major inactivation target in hepatocellular carcinoma. Cancer. 2000 Jul. 1; 89(1):60-8). DNA methylation as a control of gene expression was detected for the BRCA1 gene for breast cancer (Magdinier F, Billard L M, Wittmann G, Frappart L, Benchaib M, Lenoir G M, Guerin J F, Dante R, Regional methylation of the 5' end CpG island of BRCA1 is associated with reduced gene expression in human somatic cells FASEB J. 2000 August; 14(11): 1585-94). A correlation between methylation and non-Hodgkin's lymphoma is also assumed (Martinez-Delgado B, Richart A, Garcia M J, Robledo M, Osorio A, Cebrian A, Rivas C, Benitez J, Hypermethylation of P16ink4a and P15ink4b genes as a marker of disease in the follow-up of non-Hodgkin's lymphomas. Br J Haematol. 2000 April; 109(1):97-103). CpG methylation also brings about the progression of T-cell leukemia, which is related to a decreased expression of the CDKN2A gene (Nosaka K, Maeda M, Tamiya S, Sakai T, Mitsuya H, Matsuoka M, Increasing methylation of the CDKN2A gene is associated with the progression of adult T-cell leukemia. Cancer Res. 2000 Feb. 15; 60(4):1043-8). An increased methylation of the CpG islands was established in bladder cancer (Salem C, Liang G, Tsai Y C, Coulter J, Knowles M A, Feng A C, Groshen S, Nichols P W, Jones P A, Progressive increases in de novo methylation of CpG islands in bladder cancer. Cancer Res. 2000 May 1; 60(9):2473-6). Transcription inactivation by esophageal squamous cell carcinomas has been related to the methylation of the FHIT gene, which is associated with the progression of the disease (Shimada Y, Sato F, Watanabe G, Yamasaki S, Kato M, Maeda M, Imamura M, Loss of fragile histidine triad gene expression is associated with progression of esophageal squamous cell carcinoma, but not with the patient's prognosis and smoking history. Cancer. 2000 Jul. 1; 89(1):5-11). Neutral endopeptidase 24.11 (NEP) inactivates the increase of neuropeptides which participate in the growth of androgen-independent prostate cancer. A loss of NEP expression by hypermethylation of the NEP promotors may contribute to the development of neuropeptide-stimulated, androgen-independent prostate cancer (Usmani B A, Shen R, Janeczko M, Papandreou C N, Lee W H, Nelson W G, Nelson J B, Nanus D M, Methylation of the neutral endopeptidase gene promoter in human prostate cancers. Clin Cancer Res. 2000 May; 6(5): 1664-70). Adrenocortical tumors in adults display structural abnormalities in the tumor DNA. Among other things, these abnormalities contain an overexpression of the IGF2 gene in correlation with a demethylation of the DNA at this locus (Wilkin F, Gagne N, Paquette J, Oligny L L, Deal C, Pediatric adrenocortical tumors: molecular events leading to insulin-like growth factor II gene overexpression. J Clin Endocrinol Metab. 2000 May; 85(5):2048-56. Review). It is assumed that DNA methylations in several exons in the retinoblastoma gene contribute to the disease (Mancini D, Singh S, Ainsworth P, Rodenhiser D, Constitutively methylated CpG dinucleotides as mutation hot spots in the retinoblastoma gene (RB1). Am J Hum Genet. 1997 July; 61(1):80-7). In chronic myeloid leukemia, a relationship is suspected between the deregulation of the p53 gene and a change in the methylation pattern with progression of the disease (Guinn B A, Mills K I, p53 mutations, methylation and genomic instability in the progression of chronic myeloid leukaemia. Leuk Lymphoma. 1997 July; 26(3-4): 211-26). A connection with methylation has also been detected for acute myeloid leukemia (Melki J R, Vincent P C, Clark S J. Concurrent DNA hypermethylation of multiple genes in acute myeloid leukemia. Cancer Res. 1999 Aug. 1; 59(15):3730-40). A tumor-specific methylation site in the Wilms tumor suppressor gene has been identified (Kleymenova E V, Yuan X, LaBate M E, Walker C L, Identification of a tumor-specific methylation site in the Wilms tumor suppressor gene. Oncogene. 1998 Feb. 12; 16(6):713-20). In Burkitt's lymphoma, several promotors have a complete CpG methylation (Tao Q, Robertson K D, Manns A, Hildesheim A, Ambinder R F, Epstein-Barr virus (EBV) in endemic Burkitt's lymphoma: molecular analysis of primary tumor tissue. Blood. 1998 Feb. 15; 91(4):1373-81). It is assumed that DNA methylation plays a role in thyroid carcinoma (Venkataraman G M, Yatin M, Marcinek R, Ain K B, Restoration of iodide uptake in dedifferentiated thyroid carcinoma: relationship to human Na+/I-symporter gene methylation status. J Clin Endocrinol Metab. 1999 July; 84(7):2449-57).

Not only are many cancer diseases associated with methylation, but there are also many other diseases that are related to methylation. Investigations of inflammatory arthritis have indicated that this disease is associated with a hypomethylation of genomic DNA (Kim Y I, Logan J W, Mason J B, Roubenoff R, DNA hypomethylation in inflammatory arthritis: reversal with methotrexate. J Lab Clin Med. 1996 August; 128(2):165-72). A methylation-regulated expression has been detected for the ICF syndrome (Kondo T, Bobek M P, Kuick R, Lamb B, Zhu X, Narayan A, Bourc'his D, Viegas-Pequignot E, Ehrlich M, Hanash S M, Whole-genome methylation scan in ICF syndrome: hypomethylation of nonsatellite DNA repeats D4Z4 and NBL2). The participation of methylation is suspected in systemic lupus erythematosus (Vallin H, Perers A, Alm G V, Ronnblom L, Anti-double-stranded DNA antibodies and immunostimulatory plasmid DNA in combination mimic the endogenous IFN-alpha inducer in systemic lupus erythematosus. J Immunol. 1999 December; 163(11):6306-13); and there may also be a relationship between the Duchenne muscular dystrophy gene and a CpG-rich island (Banerjee S, Singh P B, Rasberry C, Cattanach B M, Embryonic inheritance of the chromatin organisation of the imprinted H19 domain in mouse spermatozoa. Mech Dev. 2000 February; 90(2):217-26; Burmeister M, Lehrach H, Long-range restriction map around the Duchenne muscular dystrophy gene. Nature. 1986 Dec. 11-17; 324(6097):582-5). An epigenetic effect, which involves the hypomethylation of the amyloid precursor protein, which is related to the development of the disease, is suspected in Alzheimer's disease (West R L, Lee J M, Maroun L E, Hypomethylation of the amyloid precursor protein gene in the brain of an Alzheimer's disease patient. J Mol Neurosci. 1995; 6(2):141-6). The methylation state also plays an important role at the chromosomal level. For example, in mental retardation syndromes, which are coupled with the fragility of the X chromosome, the degree of chromosomal fragility is determined by the methylation (de Muniain A L, Cobo A M, Poza J J, Saenz A. Neurologia. 1995 December; 10 Suppl 1:12-9).

A relatively new method that in the meantime has become the most widely used method for investigating DNA for 5-methylcytosine is based on the specific reaction of bisulfite with cytosine, which, after subsequent alkaline hydrolysis, is then converted to uracil, which corresponds in its base-pairing behavior to thymidine. In contrast, 5-methylcytosine is not modified under these conditions. Thus, the original DNA is converted so that methylcytosine, which originally cannot be distinguished from cytosine by its hybridization behavior, can now be detected by "standard" molecular biology techniques as the only remaining cytosine, for example, by amplification and hybridization or sequencing. All of these techniques are based on base pairing, which is now fully utilized. The prior art, which concerns sensitivity, is defined by a method that incorporates the DNA to be investigated in an agarose matrix, so that the diffusion and renaturation of the DNA is prevented (bisulfite reacts only on single-stranded DNA) and all precipitation and purification steps are replaced by rapid dialysis. (Olek, A. et al., Nucl. Acids Res. 1996, 24, 5064-5066). Individual cells can be investigated by this method, which illustrates the potential of the method. Of course, up until now, only individual regions of up to approximately 3000 base pairs long have been investigated; a global investigation of cells for thousands of possible methylation analyses is not possible. Of course, this method also cannot reliably analyze very small fragments of small quantities of sample. These are lost despite the protection from diffusion through the matrix.

An overview of other known possibilities for detecting 5-methylcytosines can be derived from the following review article: Rein, T., DePamphilis, M. L., Zorbas, H., Nucleic Acids Res. 1998, 26, 2255.

The bisulfite technique has been previously applied only in research, with a few exceptions (e.g., Zechnigk, M. et al., Eur. J. Hum. Gen. 1997, 5, 94-98). However, short, specific segments of a known gene have always been amplified after a bisulfite treatment, and either completely sequenced (Olek, A. and Walter, J., Nat. Genet. 1997, 17, 275-276) or individual cytosine positions have been detected by a primer extension reaction (Gonzalgo, M. L. and Jones, P. A., Nucl. Acids Res. 1997, 25, 2529-2531, WO-Patent 95-00669) or an enzyme step (Xiong, Z. and Laird, P. W., Nucl. Acids. Res. 1997, 25, 2532-2534). Detection by hybridization has also been described (Olek et al., WO-A 99/28,498).

Other publications which are concerned with the application of the bisulfite technique for the detection of methylation in the case of individual genes are: Xiong, Z. and Laird, P. W. (1997), Nucl. Acids Res. 25, 2532; Gonzalgo, M. L. and Jones, P. A. (1997), Nucl. Acids Res. 25, 2529; Grigg, S. and Clark, S. (1994), Bioassays 16, 431; Zeschnik, M. et al. (1997), Human Molecular Genetics 6, 387; Teil, R. et al. (1994), Nucl. Acids Res. 22, 695; Martin, V. et al. (1995), Gene 157, 261; WO-A 97/46,705, WO-A 95/15,373 and WO-A 95/45,560.

A review of the prior art in oligomer array production can be taken from the special edition of Nature Genetics that appeared in January 1999 (Nature Genetics Supplement, Volume 21, January 1999) and the literature cited therein.

Probes with multiple fluorescent labels have been used for scanning an immobilized DNA array. Particularly suitable for fluorescent labels is the simple introduction of Cy3 and Cy5 dyes at the 5'-OH of the respective probe. The fluorescence of the hybridized probes is detected, for example, by means of a confocal microscope. The dyes Cy3 and Cy5, among many others, are commercially available.

Matrix-assisted laser desorptions/ionization mass spectrometry (MALDI-TOF) is a very powerful development for the analysis of biomolecules (Karas, M. and Hillenkamp, F. (1988), Laser desorption ionization of proteins with molecular masses exceeding 10,000 daltons. Anal. Chem. 60: 2299-2301). An analyte is embedded in a light-absorbing matrix. The matrix is vaporized by a short laser pulse and the analyte molecule is transported unfragmented into the gaseous phase. The analyte is ionized by collisions with matrix molecules. An applied voltage accelerates the ions in a field-free flight tube. Ions are accelerated to varying degrees based on their different masses. Smaller ions reach the detector sooner than large ions.

MALDI-TOF spectrometry is excellently suitable for the analysis of peptides and proteins. The analysis of nucleic acids is somewhat more difficult (Gut, I. G. and Beck, S. (1995)), DNA and Matrix Assisted Laser Desorption Ionization Mass Spectrometry. Molecular Biology Current Innovations and Future Trends 1: 147-157). For nucleic acids, the sensitivity is approximately 100 times poorer than for peptides and decreases overproportionally with increasing fragment size. For nucleic acids, which have a backbone with a multiple negative charge, the ionization process via the matrix is basically less efficient. In MALDI-TOF spectrometry, the choice of matrix plays an imminently important role. Several very powerful matrices, which produce a very fine crystallization, have been found for the desorption of peptides. In the meantime, several effective matrices have been developed for DNA, but the difference in sensitivity has not been reduced thereby. The difference in sensitivity can be reduced by modifying the DNA chemically in such a way that it resembles a peptide. Phosphorothioate nucleic acids, in which the usual phosphates of the backbone are substituted by thiophosphates, can be converted by simple alkylation chemistry to a charge-neutral DNA (Gut, I. G. and Beck, S. (1995), A procedure for selective DNA alkylation and detection by mass spectrometry. Nucleic Acids Res. 23: 1367-1373). The coupling of a charge tag to this modified DNA results in an increase in sensitivity of the same order of magnitude as is found for peptides. Another advantage of charge tagging is the increased stability of the analysis in the presence of impurities, which make the detection of unmodified substrates very difficult.

Genomic DNA is obtained from DNA of cells, tissue or other test samples by standard methods. This standard methodology is found in references such as Fritsch and Maniatis, eds., Molecular Cloning: A Laboratory Manual, 1989.

Figure 1:
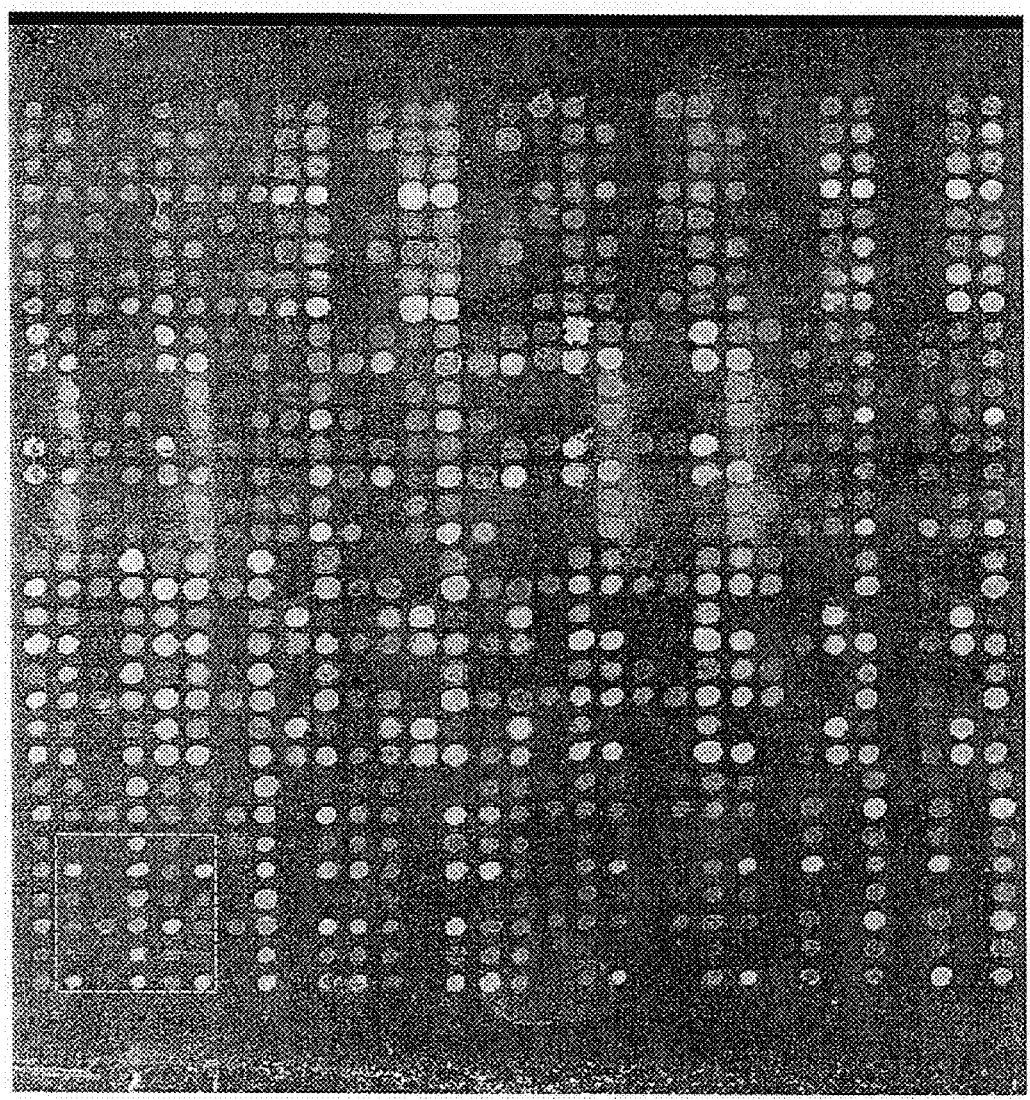
FIG. 1 shows a DNA chip after hybridization with the ELK-1 fragment. The varying intensity of the spots represent the degree of hybridization, whereby the degree of hybridization decreases from light spots to dark spots.

```
CTACTCAACAAAAACAAA (left)    (SEQ ID NO: 40717)
and

CTACTCAACGAAAACAAA (right).  (SEQ ID NO: 40718)
```

FIG. 2B shows the spotting pattern for an unknown methylation state of the tissue sample.

FIG. 2C shows the methylation state for the methylated reference sample.

The present invention will present a particularly efficient and reliable method, which permits investigating many cytosine bases in a given DNA sample simultaneously for the presence of a methyl group at position 5 by means of hybridization. Oligonucleotides and PNA oligomers are also presented for this purpose, which are particularly suitable for using the method for the diagnosis of existing diseases and of predisposition for diseases by analysis of a set of genetic and/or epigenetic parameters.

Genetic parameters in the sense of this invention are mutations and polymorphisms of the claimed nucleic acids (Seq. ID 1 to Seq. ID 40712) and additional sequences necessary for their regulation. Particularly designated as mutations are insertions, deletions, point mutations, inversions and polymorphisms and particularly preferred are SNPs (single nucleotide polymorphisms). Polymorphisms, however, can also be insertions, deletions or inversions.

Epigenetic parameters in the sense of this invention are particularly cytosine methylations and other chemical modifications of DNA bases of the claimed nucleic acids (Seq. ID 1 to Seq. ID 40712) and additional sequences necessary for their regulation. Other epigenetic parameters, for example, are the acetylation of histones, although this cannot be directly analyzed with the described method; however, it is correlated in turn with DNA methylation.

The present method serves for the detection of the degree of methylation of at least one specific cytosine in the sequence context 5'-CpG-3' of a genomic DNA sample. The method is particularly preferably used for the simultaneous detection of many different methylation positions.

The object is solved according to the invention by a method for the detection of the degree of methylation of a specific cytosine in the sequence context 5'-CpG-3' of a genomic DNA sample, which is characterized in that
a) the genomic DNA is treated, whereby the cytosine bases are converted to uracil, but not the 5-methylcytosine bases;
b) segments of the genomic DNA, which contain said specific cytosine, are amplified, whereby the amplified products are given a detectable label;
c) the amplified products are hybridized to two classes of oligonucleotides and/or PNA oligomers, each of which has at least one member;
d) the extent of hybridization of the amplified products on the two classes of oligonucleotides is determined by detection of the label of the amplified products;
e) a conclusion is made on the extent of methylation of said specific cytosine in the genomic DNA sample from the ratio of the labels detected on the two classes of oligonucleotides as a consequence of the hybridization.

A method is particularly preferred in which a hybridization of the amplified products is conducted in step c) on two classes of oligomers (oligonucleotides and/or PNA oligomers), each of which has at least one member, whereby the oligomers of the first class preferably hybridize to the sequence which arises from the chemical treatment of the genomic DNA, if said specific cytosine was present in the methylated state in the genomic DNA, and whereby the oligomers of the second class preferably hybridize to the sequence which arises from the chemical treatment of the genomic DNA if said specific cytosine was present in the unmethylated state in the genomic DNA. One of these two classes of oligomers, for example, can be formed by oligonucleotides which contain a CG in the middle, and the other class can be formed by oligonucleotides which have a TG (or a CA, in the counterstrand) in the middle. The remaining segments of the oligomer sequences should preferably be the same in the two classes. In this case, oligonucleotides of the first class hybridize to the sequence (around the specific cytosine to be investigated) if it was present in the methylated state before bisulfite conversion, and vice versa, those of the second class would hybridize to the sequence if it was present in the unmethylated state before the bisulfite conversion.

A method is also particularly preferred in which a hybridization of the amplified products is conducted in step c) on two classes of oligomers (oligonucleotides and/or PNA oligomers), each of which has at least one member, whereby the oligomers of the first class preferably hybridize to the sequence which arises after the chemical treatment of the genomic DNA if said specific cytosine was present in the methylated state in the genomic DNA and less preferably hybridize to the sequence which arises after the chemical treatment of the genomic DNA if said specific cytosine was present in the unmethylated state in the genomic DNA, and whereby the oligomers of the second class hybridize to the amplified product to be investigated essentially independently of the degree of methylation of said specific cytosine in the genomic DNA.

Correspondingly, a method is also particularly preferred in which a hybridization of the amplified products is conducted in step c) on two classes of oligomers (oligonucleotides and/or PNA oligomers), each of which has at least one member, whereby the oligomers of the first class preferably hybridize to the sequence which arises after the chemical treatment of the genomic DNA if said specific cytosine was present in the unmethylated state in the genomic DNA and less preferably hybridize to the sequence which arises after the chemical treatment of the genomic DNA if said specific cytosine was present in the methylated state in the genomic DNA, and whereby the oligomers of the second class hybridize to the amplified product to be investigated essentially independently of the degree of methylation of said specific cytosine in the genomic DNA.

Thus, in these cases, the second class of oligomers hybridizes to the amplified product without producing an essential methylation specificity, and thus accordingly, preferably to a position of the amplified product which does not correspond to methylatable cytosine positions. Thus, only the concentration of the amplified product is determined by the intensity of hybridization. In this regard, hybridization to the first class of oligonucleotides results as a function of the degree of methylation of the specific cytosine to be investigated.

It is preferred that the method is conducted not only with the genomic DNA sample, but also logically with standard DNA in which it is known whether the cytosine at said specific position is present in methylated or unmethylated state, whereby the ratios of the labels detected on the two classes of oligonucleotides, which are measured each time with the unmethylated standard DNA, serve as a calibration value for a degree of methylation of 0, and correspondingly the ratios of the labels detected on the two classes of oligonucleotides, which are measured each time with the methylated standard DNA, serve as a calibration value for a degree of methylation of 1, and these calibration values are used for the determination of the degree of methylation of the genomic DNA samples.

It is particularly preferred that additional known standard DNA samples, each of which has any known degree of methylation of said specific cytosine, are used for calibration.

The standard DNA samples used and the samples (the amplied product prepared from a genomic DNA) are each preferably given a different label. The standard DNA samples used are each preferably labeled in turn with different labels.

A method is also particularly preferred in which amplified products originating from different genomic DNA samples are provided with different labels. In this case, it is possible to measure different samples simultaneously with one set of oligonucleotides of the two classes, for example, on an oligomer array which contains oligonucleotides of the two classes.

A method is also particularly preferred, in which amplified products originating from the same genomic DNA samples are provided with different labels in order to achieve an increase of measurement accuracy by an averaging of the values obtained from different detection methods. For example, this can be carried out by labeling with different fluorescent dyes. In this case, the measurement is conducted with a fluorescence scanner, which provides several channels for the measurement of individual emission wavelengths of the fluorescent dyes.

Accordingly, a method is also particularly preferred, in which the labels are fluorescent labels.

According to the invention, it is further preferred that said label is a fluorescent label. It is preferred that said label is detected by chemiluminescence, its UV absorption or fluorescence polarization.

It is particularly preferred according to the invention that the DNA treatment in step a) is conducted with a solution of a bisulfite (=hydrogen sulfite, disulfite). A method is also particularly preferred, in which oligonucleotides are used for the amplification, which comprise a sequence segment of a chemically pretreated DNA which is at least 18 bases long according to one of the Seq. ID 1 to Seq. ID 40712. It is assured that primers complementary to the bisulfite-treated DNA are used, which can amplify regulatory regions (CpG islands) which can then be investigated with respect to methylation.

A method is also particularly preferred, in which, in a hybridization step, oligonucleotides and/or peptide nucleic acid (PNA) oligomers are used, which hybridize to a sequence segment that is at least 9 bases long of a chemically pretreated DNA according to one of the Seq. ID 1 to Seq. ID 40712 or correspond to this segment, whereby the base sequence contains at least one CpG dinucleotide and the CpG dinucleotide is found in approximately the middle third of the oligomer. These oligonucleotides are suitable for investigating specific CpG positions with respect to their degree of methylation according to the method of the invention. They preferably bind to the amplified products of treated DNA, which originates from a genomic DNA sample methylated at the respective cytosine positions.

It is also preferred that the labels are radionuclides.

It is further preferred that the labels are removable mass labels, which are detected in a mass spectrometer. It is particularly preferred according to the invention that the PCR products as a whole or their characteristic fragments are detected in the mass spectrometer and thus are clearly characterized by their mass.

It is particularly preferred according to the invention that the oligomers (oligonucleotides and/or PNA oligomers) of one class contain the sequence 5'-CG-3'.

It is particularly preferred according to the invention that the oligomers (oligonucleotides and/or PNA oligomers) of one class contain the sequence 5'-TG-3' and/or the sequence 5'-CA-3'.

It is also particularly preferred that the oligonucleotides of the first class contain the sequence 5'-CG-3' and the oligonucleotides of the second class contain the sequence 5'-TG-3' and/or the sequence 5'-CA-3'.

It is also preferred that the oligonucleotides of the first and of the second classes are immobilized on a common solid phase. It is also preferred that the oligonucleotides are arranged on a planar solid phase in a rectangular or hexagonal grid and the site of specific oligonucleotides on the solid phase is correlated with their respective sequence.

It is also particularly preferred that the oligomers of the first and second classes are immobilized on beads, which are coded with a set of separately detectable labels. The latter serve for identifying the bead, i.e., the sequence bound to the bead in question. The amplified products bound to the beads are then identified by means of other labels, which are bound to the amplified products. Instruments for conducting such measurements based on beads are offered, for example, by the Luminex company.

A method is most particularly preferred according to the invention, wherein step b) is conducted in two sub-steps as follows:
a) a PCR pre-amplification with at least one pair of primers of different sequence which hybridize nonspecifically to a DNA sample pretreated according to claim 1 and thus produce more than one amplified product in the PCR step;
b) a PCR amplification of the product formed in the pre-amplification, with primers of different sequence, which are each identical or inversely complementary to a segment of the DNA sample that has undergone pretreatment according to claim 1, and hybridize specifically to the DNA to be amplified.

In connection with this invention, hybridization is understood as a hybridization of two single DNA strands that are completely inversely complementary to each other according to Watson-Crick rules without the occurrence of an erroneous base pairing. Uracil is considered in this respect as thymine.

It is also preferred according to the invention that the amplification of several DNA segments is conducted in one reaction vessel.

It is further preferred according to the invention that a heat-stable DNA polymerase is used for the amplification. It is also particularly preferred that the primer oligonucleotides used for the amplification contain either only the bases T, A and C or the bases T, A and G.

It is also preferred that at least 10 CpG positions in different sequence context are analyzed simultaneously. It is particularly preferred that at least 50 CpG positions in different sequence context are analyzed simultaneously. It is even more particularly preferred that at least 100 CpG positions in different sequence context are analyzed simultaneously. It is even more preferred that at least 500 CpG positions in different sequence context are analyzed simultaneously. It is most preferable that at least 1000 CpG positions in different sequence context are analyzed simultaneously.

The method is preferred according to the invention, whereby the genomic DNA sample has been obtained from cell lines, blood, sputum, stool, urine, cerebrospinal fluid, tissue embedded in paraffin, for example, tissue from eyes, intestine, kidney, brain, heart, prostate, lung, breast or liver, histological slides or all other possible combinations thereof.

The use of a method according to the invention is preferred for the diagnosis and/or prognosis of adverse events for patients or individuals, whereby these adverse events belong to at least one of the following categories: undesired drug interactions; cancer diseases; CNS malfunctions, damage or disease; symptoms of aggression or behavioral disturbances; clinical, psychological and social consequences of brain damage; psychotic disturbances and personality disorders; dementia and/or associated syndromes; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disorder of the skin, the muscles, the connective tissue or the bones; endocrine and metabolic malfunction, damage or disease; headaches or sexual malfunctions.

The use of a method according to the invention is also preferred for distinguishing cell types or tissues or for investigating cell differentiation.

The subject of the present invention is a kit comprising a reagent containing bisulfite, primer oligonucleotides for the production of the amplified products and/or preferably oligonucleotides immobilized to a solid phase as well as instructions for conducting the method according to the invention. The primer oligonucleotides and the immobilized oligonucleotides, as described above, are derived from the Seq. IDs 1 to 40712.

This genomic DNA sample has been obtained preferably from cell lines, blood, sputum, stool, urine, cerebrospinal fluid, tissue embedded in paraffin, for example, tissue from eyes, intestine, kidney, brain, heart, prostate, lung, breast or liver, histological slides or all other possible combinations thereof.

In this method in the first step, a genomic DNA sample is treated in such a way that except for the 5-methylcytosine bases, all cytosine bases are converted to uracil. This chemical treatment is preferably conducted with the solution of a bisulfite (=hydrogen sulfite, disulfite). This step of the method can be conducted not only with the genomic DNA sample, but also preferably and logically with standard DNA in which it is known whether the cytosine at said specific position is present in methylated or unmethylated state.

In the second step of the method, the segments of the genomic DNA that contain said specific cytosine are amplified. This step can be particularly preferably conducted in two sub-steps:
1. First, a PCR pre-amplification is conducted with at least one pair of primers of different sequence, which hybridize to a chemically pretreated DNA. This treatment was chemically conducted in such a way that the cytosine bases were converted to uracil, but not the 5-methylcytosine bases.
2. A PCR amplification of the product formed in the pre-amplification is conducted with primers of different sequence. These primers are identical or inversely complementary to a segment of the chemically pretreated DNA and specifically hybridize to the DNA to be amplified. The amplified products preferably contain a detectable label.

In the following third step of the method, a hybridization of the amplified products takes place on preferably two classes of oligonucleotides, each of which has at least one member. In a particularly preferred variant of the method, the oligonucleotides of the first class contain the sequence 5'-CG-3' and the oligonucleotides of the second class contain the sequence 5'-TG-3' and/or the sequence 5'-CA-3'. The oligonucleotides of the first and the second classes are preferably immobilized on a common solid phase. The oligonucleotides are arranged on a planar solid phase in a rectangular or hexagonal grid and the site of specific oligonucleotides on the solid phase is correlated with their respective sequence.

The oligonucleotides of the first class preferably hybridize to the sequence which arises from the chemical treatment of the genomic DNA if said specific cytosine was present in the methylated state in the genomic DNA. The oligonucleotides of the second class preferably hybridize to the sequence which arises from the chemical treatment of the genomic DNA if said specific cytosine was present in the unmethylated state in the genomic DNA.

The amplification of several DNA segments is particularly preferably conducted in one reaction vessel. The amplification is preferably conducted with the polymerase chain reaction (PCR), wherein a heat-stable DNA polymerase is preferably used.

The primer oligonucleotides used for the amplification contain preferably either only the bases T, A and C or the bases T, A and G.

In the fourth step of the method, the extent of hybridization of the amplified products on the two classes of oligonucleotides is determined by detection of the labels of the amplified products. The labels are particularly preferably fluorescent labels, radionuclides, or removable mass labels, which are detected in a mass spectrometer.

The labels are preferably also detected by chemiluminescence, UV absorption or fluorescence polarization. The PCR products can also preferably be detected as a whole or as their characteristic fragments in the mass spectrometer. Thus the PCR products are clearly characterized by their mass.

In the last step of the method, a conclusion is made on the extent of methylation of said specific cytosine in the genomic DNA sample from the ratio of the labels detected on the two classes of oligonucleotides as a consequence of the hybridization.

The ratios of the labels detected on the two classes of oligonucleotides, which are measured each time with the unmethylated standard DNA, preferably serve as a calibration value for a degree of methylation of 0.

Correspondingly, the ratios of the labels detected on the two classes of oligonucleotides, which are measured each time with the methylated standard DNA, preferably serve as a calibration value for a degree of methylation of 1.

The calibration values are particularly preferably used for the determination of the degree of methylation of the genomic DNA samples.

Preferably, additional known standard DNA samples, each of which has any known degree of methylation of said specific cytosine, are also used for the calibration.

The method is further characterized in that preferably at least 10 CpG positions in different sequence context are analyzed simultaneously. In addition, preferably at least 50 CpG positions in different sequence context can be analyzed simultaneously. It is also preferred that at least 100 CpG positions in different sequence context are analyzed simultaneously. The simultaneous analysis of at least 500 CpG positions in different sequence context is very much preferred. The simultaneous analysis of at least 1000 CpG positions in different sequence context is finally particularly preferred.

The described method is preferably used for the diagnosis and/or prognosis of adverse events for patients or individuals, whereby these adverse events belong to at least one of the following categories: undesired drug interactions; cancer diseases; CNS malfunctions, damage or disease; symptoms of aggression or behavioral disturbances; clinical, psychological and social consequences of brain damage; psychotic disturbances and personality disorders; dementia and/or associated syndromes; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disorder of the skin, the muscles, the connective tissue or the bones; endocrine and metabolic malfunction, damage or disease; headaches or sexual malfunctions.

The present method is particularly preferably used for distinguishing cell types or tissues or for investigating cell differentiation.

By determining the hybridization ratios between the two classes of oligonucleotides utilized (e.g., containing CG/TG), the method is not dependent on the intensity of the total hybridization of unknown tissue samples.

Unmethylated and methylated reference samples are utilized as standards for calibrating unknown tissue samples.

A component of this method is also a kit, which comprises a reagent containing bisulfite, primer oligonucleotides for the production of amplified products and/or preferably oligonucleotides immobilized on a solid phase. The oligonucleotides (first class) comprise the sequence 5'-CG-3'. The oligonucleotides (second class) comprise the sequence 5'-TG-3' and/or the sequence 5'-CA-3'. Instructions for conducting the method are also included in the kit.

The subject of the present invention is also nucleic acids that are particularly suitable for conducting the method.

The subject of the invention is also a set of at least 10 oligomer probes (oligonucleotides and/or PNA oligomers), which serve for the detection of the cytosine methylation state in chemically pretreated genomic DNA (Seq. ID 1 to Seq. ID 40712). The analysis of a set of genetic and/or epigenetic parameters for the diagnosis of existing diseases or for the diagnosis of predisposition to specific diseases is possible with these probes.

The subject of the present invention is also a sequence segment of a treated DNA which is at least 18 bases long according to one of the Seq. ID 1 to Seq. ID 40712. These segments of 18 base pairs in length comprised of Seq. ID 1 to Seq. ID 40712 are utilized for the amplification of the treated genomic DNA. Oligomers with a length of at least 9 nucleotides are used as detectors of these segments.

The oligomers preferably contain at least one CpG dinucleotide. The cytosine of the corresponding CpG dinucleotide is found in approximately the middle third of the oligomer. It is a deciding factor that at least one oligonucleotide from Seq. ID 1 to Seq. ID 40712 is present in the respective set of oligomers for at least each of the CpG dinucleotides.

The oligomers are preferably produced on a support material in a fixed arrangement, whereby at least one oligomer is coupled to a solid phase. Methods for binding oligomer probes to solid phases are known to the person of average skill in the art.

It is also important in this connection that it is not individual CpG dinucleotides, but the large number of CpG dinucleotides present in the sequences, which must be analyzed for the diagnosis of genetic and/or epigenetic parameters of the claimed nucleic acids (Seq. ID 1 to Seq. ID 40712). In a particularly preferred variant of the method, all of the CpG dinucleotides present in the sequences are to be investigated.

It is further preferred that all oligomer probes have the same length. In addition, all 18-mer which have a CpG dinucleotide in the center and which hybridize to one of the Seq. ID 1 to Seq. ID 40712 without erroneous base pairing are particularly preferred.

In another preferred variant of the method, at least ten of the oligomers are used for the detection of the cytosine methylation state and/or of single nucleotide polymorphisms (SNPs) in chemically pretreated genomic DNA.

The oligomers are preferably used for the diagnosis of undesired drug interactions; cancer diseases; CNS malfunctions, damage or diseases; symptoms of aggression or behavioral disturbances; clinical, psychological and social consequences of brain lesions; psychotic disturbances and personality disorders; dementia and/or associated syndromes; cardiovascular disease; malfunction, damage or disorder of the gastrointestinal tract; malfunction, damage or disorder of the respiratory system; lesion, inflammation, infection, immunity and/or convalescence; malfunction, damage or disorder of the body as an abnormality in the development process; malfunction, damage or disorder of the skin, the muscles, the connective tissue or the bones; endocrine and metabolic malfunction, damage or disorder; headaches and sexual malfunctions, by analysis of methylation patterns.

Also, of the nucleic acids or considerable segments thereof listed in the sequence protocol (Seq. ID 1 to Seq. ID 40712), preferably at least one will be used for the analysis of a set of genetic and/or epigenetic parameters for the diagnosis of existing disorders or for the diagnosis of predisposition for specific disorders.

The person of average skill in the art understands that the oligomers fulfill the same objective when thymine is exchanged for uracil.

The genomic DNA to be analyzed is obtained preferably from the usual sources for DNA, such as, e.g., cell lines, blood, sputum, stool, urine, cerebrospinal fluid, tissue embedded in paraffin, for example, tissue from eyes, intestine, kidney, brain, heart, prostate, lung, breast or liver, histological slides and all other possible combinations thereof.

The subject of the present invention is also nucleic acids containing a sequence segment which is at least 18 bases long of a chemically pretreated DNA, according to one of the Seq. ID 1 to Seq. ID 40712.

The subject of the present invention is also an oligomer (oligonucleotide or peptide nucleic acid (PNA) oligomer) for the detection of the cytosine methylation state in chemically pretreated DNA, each containing at least one base sequence with a length of at least 9 nucleotides, which hybridizes to a chemically pretreated DNA (Seq. ID 1 to Seq. ID 40712). It is also preferred according to the invention that the base sequence contains at least one dinucleotide. It is also preferred that the cytosine of the CpG dinucleotide is found in approximately the middle third of the oligomer.

The subject of the invention is also a set of oligomers according to the invention, containing at least one oligomer for at least one of the CpG dinucleotides of one of the sequences of Seq. ID 1 to Seq. ID 40712. A set of oligomers containing at least one oligomer for each of the CpG dinucleotides of one of the sequences of Seq. ID 1 to Seq. ID 40712 is preferred.

The subject of the present invention is also a set of at least two nucleic acids, which are utilized as primer oligonucleotides for the amplification according to the invention of at least one of the Seq. ID 1 to Seq. ID 40712 or segments thereof. It is preferred that at least one oligonucleotide is bound to a solid phase.

The subject of the present invention is also a set of oligomer probes for the detection of the cytosine methylation state and/or of single nucleotide polymorphisms (SNPs) in chemically pretreated genomic DNA according to one of the Seq. ID 1 to Seq. ID 40712, containing at least ten of the above-named oligomers according to the invention.

The subject of the present invention is also a method for the production of an arrangement of different oligomers (an array) fixed on a support material for the analysis of disorders related to the methylation state of the CpG dinucleotides of one of the Seq. ID 1 to Seq. ID 40712, in which at least one oligomer according to the invention is coupled to a solid phase.

The subject of the invention is also arrangements of different oligomers (array) bound to a solid phase.

The subject of the present invention is also an array of different oligonucleotide and/or PNA oligomer sequences whereby these are arranged on a planar solid phase in the form of a rectangular or hexagonal grid. It is preferred that the solid phase surface is comprised of silicon, glass, polystyrene, aluminum, steel, iron, copper, nickel, silver, or gold.

According to the invention, a DNA and/or PNA array is also for the analysis of disorders related to the methylation state of genes, which contains at least one nucleic acid as described above according to the invention.

The following examples explain the invention.

EXAMPLE 1

Production of Unmethylated and Methylated DNA and Bisulfite Treatment

For the production of methylated DNA, human genomic DNA was treated with S-adenosylmethionine and CpG methylase (Sssl, New England Biolabs,) according to the information of the manufacturer. For the production of unmethylated DNA, the gene fragment ELK-1 (Accession number ep59011) was amplified by means of PCR with the primers GCTCTATGGTCTTGTCTAACCGTA (SEQ ID NO: 40713) and AGGTGGTGGTGGCGGTGG (SEQ ID NO: 40714), starting from human genomic DNA. The unmethylated and methylated DNA, which was prepared in this way, as well as also the human genomic DNA was treated with the use of bisulfite (hydrogen sulfite, disulfite), such that all cytosines unmethylated at the 5-position of the base are changed so that a base that is different with respect to base pairing behavior is formed, whereas the cytosines that are methylated in the 5-position remain unchanged. If bisulfite in the concentration range between 0.1 M and 6 M is used for the reaction, then an addition occurs at the unmethylated cytosine bases. Also, a denaturing reagent or solvent as well as a radical trap must be present. A subsequent alkaline hydrolysis then leads to the conversion of unmethylated cytosine nucleobases to uracil. This converted DNA serves for the detection of methylated cytosines.

EXAMPLE 2

Production of Cy5-Labeled Gene Probes

Starting with DNA samples treated with bisulfite, a defined fragment of 529 bp in length from the promoter region of the ELK-1 gene (Accession number ep59011) was amplified. The amplification is conducted with the primer oligonucleotides ATGGTTTTGTTTAATYGTAGAGTTGTTT (SEQ ID NO: 40715) and TAAAC-CCRAAAAAAAAAAAACCCAATAT (SEQ ID NO: 40716). By using primer oligonucleotides that are labeled with the fluorescent dye Cy5, the fragment is directly labeled in the PCR. (1) Unmethylated DNA, (2) methylated DNA and (3) human genomic DNA treated with bisulfite (hydrogen sulfite, disulfite) are used as the matrix DNA. Then these three different DNA fragments are investigated in separate hybridizations for their degree of methylation at a specific CpG position.

EXAMPLE 3

Conducting the Hybridization and Evaluating a Hybridized DNA Chip

Figure 2:
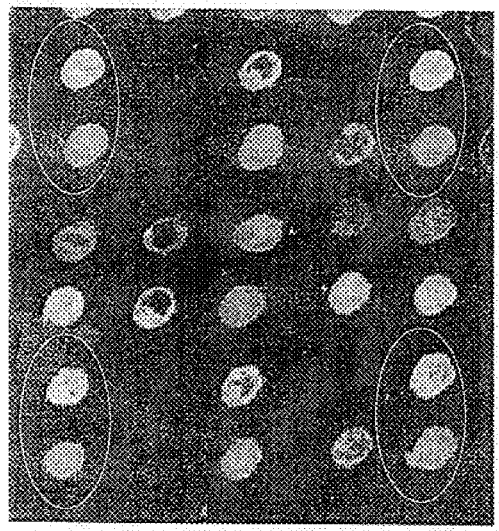
FIG. 2A shows an excerpted image from FIG. 1. The spotted pairs of oligonucleotides are circled in white to clarify the hybridization diagram.
Figure 2:
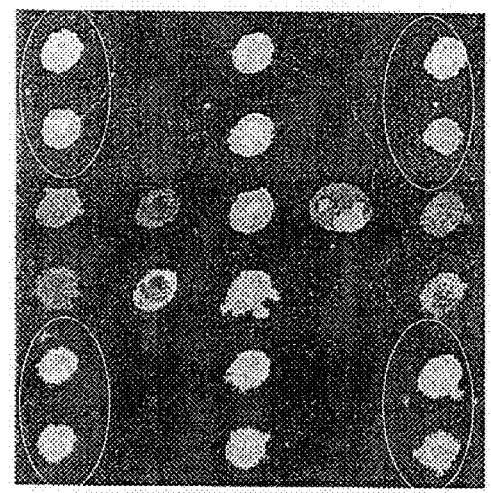
Figure 2:
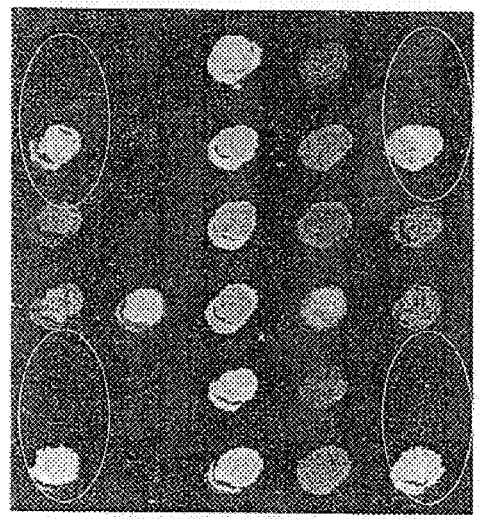

The gene probes prepared in Example 2 are hybridized to a DNA chip. First, oligonucleotides are immobilized on the chip. The oligonucleotide sequences are derived from the amplified fragment of the ELK-1 gene named in Example 2, and represent the CG dinucleotide, including the immediate surroundings. The length of the oligonucleotides amounts to 14-22 nucleotides; the position of the CG dinucleotide within the oligonucleotide is variable. After the hybridization, the DNA chip is scanned (see FIG. 1) and the hybridization signals are numerically evaluated (data not shown). The result of the hybridization for the oligonucleotides CTACTCAACGAAAACAAA (SEQ ID NO: 40717) and CTACTCAACAAAAACAAA (SEQ ID NO: 40718) is shown in FIG. 1 and FIG. 2. CTACTCAACGAAAACAAA (SEQ ID NO: 40717) preferably hybridizes if the cytosine of the ELK-1 fragment, which is found at position 103 of the amplified product, is methylated; CTACT-CAACAAAAACAAA (SEQ ID NO: 40718) hybridizes if this cytosine is unmethylated.

A DNA chip is shown in FIG. 1 after hybridization with the ELK-1 fragment. The pseudo-color image as it is produced after scanning is shown. Unlike the black-and-white illustration shown here, a color image is produced by the scanner. The intensity of the different colors represent the degree of hybridization, whereby the degree of hybridization decreases from red (this can be recognized as light spots in FIG. 1) to blue (recognized as dark spots in FIG. 1).

FIG. 2 A shows an excerpted image from FIG. 1. The spotted pairs of oligonucleotides are circled in white to clarify the hybridization diagram: ctactcaacaaaaacaaa (left) (SEQ ID NO: 40717) and ctactcaacgaaaacaaa (right) (SEQ ID NO: 40718).

The excerpted image of FIG. 2 B shows the spotting pattern for an unknown methylation state of the tissue sample and the excerpted image of FIG. 2 C shows the methylation state for the methylated reference sample.

TABLE 1

| Sequence of the detection oligomer | Sample A (unmethylated) Fluorescence (counts) | Mean | Sample B (unknown) Fluorescence (counts) | Mean | Sample C (methylated) Fluorescence (counts) | Mean |
|---|---|---|---|---|---|---|
| ctactcaacgaaaacaaa (SEQ ID NO: 40717) | 3352 | | 6102 | | 6002 | |
| ctactcaacgaaaacaaa (SEQ ID NO: 40717) | 2950 | | 6775 | | 7898 | |
| ctactcaacgaaaacaaa (SEQ ID NO: 40717) | 4196 | | 6360 | | 7485 | |
| ctactcaacgaaaacaaa (SEQ ID NO: 40717) | 5181 | | 5521 | | 11401 | |
| | | 3920 | | 6190 | | 8197 |
| ctactcaacaaaaacaaa (SEQ ID NO: 40718) | 20577 | | 7074 | | 7290 | |
| ctactcaacaaaaacaaa (SEQ ID NO: 40718) | 19709 | | 9171 | | 9985 | |
| ctactcaacaaaaacaaa (SEQ ID NO: 40718) | 24130 | | 7603 | | 9286 | |
| ctactcaacaaaaacaaa (SEQ ID NO: 40718) | 21601 | | 9434 | | 12435 | |
| | | 21504 | | 8321 | | 9749 |
| CG/CA | | 0.28 | | 0.74 | | 0.84 |

The mean is indicated each time for a wavelength of 635 nm. Column A gives the values for the unmethylated sample and column B for an unknown methylation state of a tissue sample and column C gives the values for the methylated reference sample. The CG/CA ratios represent the methylation state of the respective sample. The value of 0.74 shows that the sample is basically present in methylated form.

EXAMPLE 4

The following example relates to a fragment of the hMLH1 gene associated with hereditable non-polyposis colorectal cancer, in which a specific CG position is investigated for methylation.

In the first step, a genomic sequence is treated with the use of bisulfite (hydrogen sulfite, disulfite) in such a way that all of the unmethylated cytosines at the 5-position of the base are modified such that a base that is different in its base pairing behavior is formed, while the cytosines that are methylated in the 5-position remain unchanged. If bisulfite in the concentration range between 0.1 M and 6 M is used for the reaction, then an addition occurs at the unmethylated cytosine bases. Also, a denaturing reagent or solvent as well as a radical trap must be present. A subsequent alkaline hydrolysis then leads to the conversion of unmethylated cytosine nucleobases to uracil. This converted DNA serves for the detection of methylated cytosines. In the second step of the method, the treated DNA sample is diluted with water or an aqueous solution. A desulfonation of the DNA (10-30 min, 90-100° C.) at alkaline pH is then preferably conducted. In the third step of the method, the DNA sample is amplified in a polymerase chain reaction, preferably with a heat-stable DNA polymerase. In the present Example, cytosines of the hMLH1 gene, here from a 1551-bp-long 5'-flanking region, are investigated. A defined fragment of 719-bp length is amplified for this purpose with the specific primer oligonucleotides AGCAACACCTCCATGCACTG (SEQ ID NO: 40719) and TTGATTGGACAGCTTGAATGC (SEQ ID NO: 40720). This amplified product serves as a sample, which hybridizes to an oligonucleotide that has been previously bound to a solid phase, with the formation of a duplex structure, for example, GAAGAGCGGACAG (SEQ ID NO: 40721), whereby the cytosine to be detected is found at position 588 of the amplified product. The detection of the hybridization product is based on primer oligonucleotides fluorescently labeled with Cy3 and Cy5, which were used for the amplification. A hybridization reaction of the amplified DNA with the oligonucleotide occurs only if a methylated cytosine was present at this site in the bisulfite-treated DNA. Thus the methylation state of the respective cytosine to be investigated decides the hybridization product.

EXAMPLE 5

Production of Bisulfite-Modified DNA with Agarose Beads

In the present experiment, starting with DNA treated with bisulfite, a defined fragment of 529 bp in length from the promoter region of the ELK-1 gene (Accession number ep59011) is amplified. By using primer oligonucleotides ATGGTTTTGTTTAATYGTAGAGTTGTTT (SEQ ID NO: 40715) and TAAACCCRAAAAAAAAAAAACCCAATAT (SEQ ID NO: 40716), which are labeled with the fluorescent dye ALEXA 488, the fragment is directly labeled in the PCR. Oligonucleotides of the first class (here, for example, ATTAATAGCGTTTTGGTT, SEQ ID NO: 40722) and of the second class (here: for example, ATTAATAGT- GTTTTGGTT, SEQ ID NO: 40723) are immobilized at the surface of beads, which are distinguished by an individual color coding. In a following step, the amplified products of the ELK-1 gene, which were prepared with the above-named primer oligonucleotides, are combined with a mixture of both classes of beads, whereby the amplified products hybridize to the immobilized oligonucleotides, here, for example, ATTAATAGCGTTTTGGTT (SEQ ID NO: 40722) and ATTAATAGTGTTTTGGTT (SEQ ID NO: 40723), whereby the C or T to be detected is found each time at position 476 of the amplified product. Then the beads are separated, identified by fluorescence measurement based on their color coding and the degree of hybridization is determined by measurement of the fluorescent intensities, which are specific to the fluorescent dye ALEXA 488.

EXAMPLE 6

Use of Multiple Dyes for Internal Calibration

Starting with bisulfite-treated DNA, a defined fragment of 529-bp length from the promoter region of the ELK-1 gene is amplified. The fragment is labeled directly in the PCR by use of the fluorescently labeled primer oligonucleotides ATGGTTTTGTTTAATYGTAGAGTTGTTT (SEQ ID NO: 40715) and TAAACCCRAAAAAAAAAAACCCAATAT (SEQ ID NO: 40716). For the PCR reaction, which is conducted on a thermocycler (Eppendorf GmbH), 10 ng of bisulfite-treated DNA, 6 μmol of each primer, 200 μM of each dNTP, 1.5 mM MgC12 and 1 U of HotstartTaq (Qiagen AG) are used. The other conditions are selected following the manufacturer's information. For the amplification, a denaturing is conducted for 14 min at 96° C., followed by 39 cycles with the conditions: 60 sec at 96° C., 45 sec at 55° C. and 75 sec at 72° C. In conclusion, an elongation is conducted for 10 min at 72° C. In the present case, the samples to be investigated, here the tissue of healthy and sick persons, are labeled with the Cy2 dye. For the internal calibration of the methylation state, primer oligonucleotides are used for the amplification of samples for the calibration, which are labeled with the fluorescent dyes Cy3 and Cy5. The amplified products from the samples for the calibration represent a known methylation state, on the one hand, a state of one-hundred percent methylation, and, on the other hand, an unmethylated state. Since in this method, the ratios of the color intensities of the fluoresent dyes, which are measured with the use of the ScanArray 4000XL, Packard BioScience-BioChip Technologies, are calculated for two classes of oligonucleotides, here, for example, ATTAATAGCGTTTTGGTT (SEQ ID NO: 40722) and ATTAATAGTGTTTTGGTT (SEQ ID NO: 40723), wherein the C or T to be detected is found each time at position 476 of the amplified product, the ratio of methylated to unmethylated state of the unknown sample can be determined.

EXAMPLE 7

Use of Multiple Dyes for Increasing the Sample Throughput Volume and for Increasing the Complexity of the Analysis.

The present experiment serves for the purpose of analyzing different samples in a single hybridization step and in this way increasing the sample throughput volume. For this purpose, a defined fragment of 529-bp length from the promoter region of the ELK-1 gene taken from each of four individuals and, starting with the bisulfite-treated DNA, is amplified with the primer oligonucleotides ATGGTTTT-GTTTAATYGTAGAGTTGTTT (SEQ ID NO: 40715) and TAAACCCRAAAAAAAAAAACCCAATAT (SEQ ID NO: 40716). These fragments originating from four individuals are labeled with the four different fluorescent dyes Cy3, Cy5, Cy2 and Cy7 and hybridized to immobilized oligonucleotides, here, for example, ATTAATAGCGTTTTGGTT and ATTAATAGTGTTTTGGTT, whereby the C or T to be detected is found each time at position 476 of the amplified product. The samples with different fluorescent labels are then analyzed at different wavelengths without a mutual interference based on the fluorescent dye.

On the other hand, it is also possible to produce different sets of fragments from one DNA sample, which are labeled with different dyes, here Cy2, Cy3 and Cy5. If a set of oligonucleotide probes for 64 genes (set 1) is immobilized on a chip, then the specificity is sufficient in order to analyze 64 fragments, e.g., labeled with Cy3, independent of one another. Due to the fact that samples of set 1 are labeled here with the fluorescent dye Cy3 and samples of set 2 are labeled with the fluorescent dye Cy5 (and set 3 with Cy2), the detection of the methylation state via measuring the fluorescent intensities of the fragments of set 1 is not influenced by the fluorescently labeled amplified products of sets 2 and 3 (and vice versa). Therefore, despite the increased complexity of the amplified products, it is possible to produce data that are equally reliable to those for a complexity of 64 amplified products.

EXAMPLE 8

Use of Multiple Dyes for Verifying Experimental Reproducibility

In the present experiment, the same PCR amplified products are labeled with four different fluorescent dyes and these are verified by a 4× redundancy. For this purpose, starting from bisulfite-treated DNA, a a defined fragment of 529-bp length from the promoter region of the ELK-1 gene is amplified with the primer oligonucleotides ATGGTTTT-GTTTAATYGTAGAGTTGTTT (SEQ ID NO: 40715) and TAAACCCRAAAAAAAAAAACCCAATAT (SEQ ID NO: 40716), and hybridized to immobilized oligonucleotides, here, for example, ATTAATAGTGTTTTGGTT (SEQ ID NO: 40722) and ATTAATAGTGTTTTGGTT (SEQ ID NO: 40723), whereby the C or T to be detected is found each time at position 476 of the amplified product. The ratios of samples with different fluorescent labels are compared by employing primer oligonucleotides fluorescently labeled with Cy3, Cy5, Cy2 and Cy7, and in this way a higher experimental reliability is achieved.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09719131B2). An electronic copy of the "Sequence Listing" will also be available from the USPTO upon request and payment of the fee set forth in 37 CFR 1.19(b)(3).

The invention claimed is:

1. A kit, comprising:
   (a) a reagent containing bisulfite;
   (b) primer or probe oligonucleotides for detection of the cytosine methylation state of the Septin 9 gene, where the primer or probe oligonucleotides each individually comprise at least 14 contiguous bases of a portion of a sequence selected from the group consisting of SEQ ID NOs: 12693, 12694, 12695, and 12696, wherein the portion of the sequence comprises at least one CpG dinucleotide, and wherein at least one of the primer or probe oligonucleotides is a peptide nucleic acid (PNA) oligomer or is bound to a solid support or to a fluorescent or radionuclide label; and
   (c) instructions for conducting a method for detecting the degree of methylation of a genomic DNA sample.

2. An isolated oligonucleotide or peptide nucleic acid (PNA) oligomer for the detection of the cytosine methylation state of the Septin 9 gene, wherein the isolated oligonucleotide or PNA oligomer comprises at least 14 contiguous bases of a portion of a sequence selected from the group consisting of SEQ ID NOS: 12693, 12694, 12695, and 12696, wherein the portion of the sequence comprises at least one CpG dinucleotide, and wherein the isolated oligonucleotide is between 14-22 nucleotides in length and is bound to a solid support or to a fluorescent or radionuclide label.

3. The oligonucleotide or PNA oligomer of claim 2, wherein the cytosine of the CpG dinucleotide is found in approximately the middle third of the oligonucleotide or PNA oligomer.

4. The oligonucleotide or PNA oligomer of claim 2, wherein the isolated PNA oligomer is between 14-22 nucleotides in length.

5. The oligonucleotide or PNA oligomer of claim 2, wherein the isolated oligonucleotide or PNA oligomer is the PNA oligomer.

6. An isolated oligonucleotide for the detection of the cytosine methylation state of the Septin 9 gene, wherein the isolated oligonucleotide comprises at least 14 contiguous bases of a portion of a sequence selected from the group consisting of SEQ ID NOS: 12693, 12694, 12695, and 12696, wherein the portion of the sequence comprises at least one CpG dinucleotide, and wherein the isolated oligonucleotide is between 14-22 nucleotides in length and is bound to a fluorescent or radionuclide label.

7. The oligonucleotide of claim 6, wherein the cytosine of the CpG dinucleotide is found in approximately the middle third of the oligonucleotide.

\* \* \* \* \*